United States Patent
Dumberger et al.

(10) Patent No.: US 6,318,153 B1
(45) Date of Patent: Nov. 20, 2001

(54) NON-CONTACT FILM THICKNESS GAUGING SENSOR

(75) Inventors: Martin Dumberger, Fürstenzell; Axel Seikowsky, Pfarrkirchen; Martin Sellen; Karl Wisspeintner, both of Ortenburg, all of (DE)

(73) Assignee: Micro-Epsilon Messtechnik GmbH & Co. KG, Ortenburg (DE)

( * ) Notice: Subject to any disclaimer, the term of this patent is extended or adjusted under 35 U.S.C. 154(b) by 0 days.

(21) Appl. No.: 09/269,444

(22) PCT Filed: Sep. 30, 1996

(86) PCT No.: PCT/DE96/01867

§ 371 Date: Mar. 26, 1999

§ 102(e) Date: Mar. 26, 1999

(87) PCT Pub. No.: WO98/14751

PCT Pub. Date: Apr. 9, 1998

(51) Int. Cl.[7] ............... G01B 13/04; G01L 5/04
(52) U.S. Cl. ............... 73/37.6; 73/159
(58) Field of Search ............... 73/37.5, 37.6, 73/37.7, 159, 866.5

(56) References Cited

U.S. PATENT DOCUMENTS

| 3,358,225 | | 12/1967 | Peugeot . | |
|---|---|---|---|---|
| 3,802,086 | * | 4/1974 | Walker | 73/37.5 |
| 3,818,327 | * | 6/1974 | Alexander | 324/231 |
| 3,854,322 | * | 12/1974 | Wood et al. | 73/37.5 |
| 3,884,076 | | 5/1975 | Studer . | |
| 3,894,423 | * | 7/1975 | Messmer | 73/37.5 |
| 4,292,838 | * | 10/1981 | Larsen | 73/37.7 |
| 4,339,714 | | 7/1982 | Ellis . | |
| 4,433,571 | * | 2/1984 | Snow, Jr. | 73/37.5 |
| 4,434,649 | * | 3/1984 | Williams | 73/37.7 |
| 4,528,507 | * | 7/1985 | Domin et al. | 324/229 |
| 5,243,849 | * | 9/1993 | Williams | 73/37.7 |
| 5,616,853 | * | 4/1997 | Oshumi | 73/37.5 |
| 5,789,661 | * | 8/1998 | Fauque et al. | 73/37.5 |

FOREIGN PATENT DOCUMENTS

| 195 11 939 | 10/1996 | (DE) . |
|---|---|---|
| 0 078 096 | 5/1983 | (EP) . |
| WO 91 15730 | 10/1991 | (WO) . |

* cited by examiner

Primary Examiner—Thomas P. Noland
Assistant Examiner—Jay L. Politzer
(74) Attorney, Agent, or Firm—Alston & Bird LLP

(57) ABSTRACT

A sensor (1) is proposed for noncontacting thickness gauging on films (2), in particular blown films, with a sensor head (3) and a mount (4) for the sensor head (3), which provides reliable measuring results despite transportation-caused movements of the film (2), and which is particularly suitable for a continuous quality control during the production process. In accordance with the invention, the sensor head (3) comprises at least one noncontacting sensor element for gauging the thickness in accordance with the physical properties of the film (2). Furthermore, the position of the sensor head (3) is adjustable such that the sensor head (3) is held during the entire measuring process at a predeterminable, at least largely constant distance from the film (2).

13 Claims, 4 Drawing Sheets

NON-CONTACT FILM THICKNESS GAUGING SENSOR

BACKGROUND OF THE INVENTION

The invention relates to a sensor for noncontacting thickness gauging on films, in particular blown films, with a sensor head and a mount for the sensor head, the sensor head comprising at least one noncontacting sensor element for gauging the thickness in accordance with the physical properties of the film.

Large varieties of sensors for noncontacting thickness gauging are known from practice. For example, the thickness of film tapes is monitored during production with two oppositely arranged displacement measuring sensors with the film tape advancing between the displacement measuring sensors. In practice, this sensor arrangement is problematic, since displacement measuring sensors normally display a nonlinear behavior. Fluttering of the film tape being monitored, different tape thicknesses, or the movement of the tapes toward or away from the displacement measuring sensors will cause measuring errors that are due to the nonlinear behavior of the displacement measuring sensors in the measuring range.

For thickness measurements on blown films the known sensor arrangement is totally unsuited, since a blown film cannot be guided between the two displacement measuring sensors. For this reason, it has until now been common practice to use sensing sensor arrangements for gauging the thickness of blown films. However, since thickness gauging should not occur during a stage of the production process, when the film material is still soft and deformable, a sensing thickness measurement will always leave sliding marks of the sensor head, unless it even leads to damage to the film tape and to tearing of same in the extreme case.

It is therefore the object of the invention to provide a sensor for gauging the thickness on films, which makes it possible to perform on the one hand a noncontacting thickness measurement, in particular also on blown films, and which largely prevents on the other hand measuring errors that are caused by the movement of film during the production process.

SUMMARY OF THE INVENTION

The above and other objects and advantages of the present invention are achieved by the provision of a sensor which comprises a sensor head which includes a bottom plate, and at least one non-contacting sensor element mounted on the bottom plate and which is capable of gauging the thickness of the film from the physical properties of the film when the film is located adjacent and spaced below the bottom plate. A plurality of gas outlets extend through the bottom plate and are directed toward the film, with the outlets arranged to encircle the sensor element. A mount is provided for mounting the sensor head for movement toward and away from the film, and means is provided for adjusting the position of the sensor head in the mount. The adjusting means comprises a gas supply connected to the gas outlets so that a gas flow is directed toward the film, and thus a fine adjustment of the spacing between the sensor head and the film occurs automatically by means of the gas flow. Also, the gas flow generates a vacuum about the sensor element which acts to lift the film without contacting the bottom plate so that during the measuring procedure a predeterminable and essentially constant relative position is maintained between the bottom plate and the film in spite of any random movement of the film toward and away from the bottom plate.

It has been recognized by the present invention that in particular for gauging films during the production process it is desirable to prefer noncontacting sensor elements, since same are by no means able to influence the deforming process of the film material. It has further been recognized that the selection of the sensor element or of a suitable measuring method depends essentially on the physical properties of the film material. Finally, it has also been recognized that in the case of all noncontacting sensor elements a defined distance between the sensor element and the measuring object, in this instance the film, is prerequisite for an as reliable acquisition as possible of measuring data. Proceeding from this prerequisite, it has been recognized that a defined distance between the sensor head or sensor element and the film does not necessarily require that the film be secured in position relative to the sensor head, but that it is necessary to maintain only a defined relative position between the film and the sensor head. The present invention therefore suggests that the position of the sensor head be dynamically adapted to the position of the film. Thus, the position of the sensor head is to be adjusted to the expected position of the film not only one time, but is to be adjustable such that the sensor head maintains during the entire measuring process a predeterminable, at least largely constant distance from the film. This means that the present invention is directed to securing not only exclusively the position of the film, but also to adjusting the position of the sensor head to the movement of the film.

In a particularly advantageous embodiment of the sensor according to the invention, the sensor element furnishes distance-independent measuring results in a small distance range between the sensor head and the film. In this manner, it is possible to neglect minor inaccuracies in the position adjustment of the sensor head. Likewise, a certain time shift between the movement of the film and the movement of the sensor head will not negatively affect the measuring accuracy of the sensor even when the spacing between the sensor head and the film lies within the distance range of the distance-independent measuring results.

In particular for gauging the thickness on blown films, sensor elements operating by capacitance have been successful. Blown films are normally made of a plastic material that influences as a dielectric the capacitance of a capacitor arrangement. Contrary thereto, inductive sensor elements offer themselves in the case of an electrically conductive film material. Such materials interact with the field of a measuring coil and thereby influence the inductance of the measuring coil. Noncontacting thickness measurements may also be made with the use of optical sensor elements, which will require a corresponding measuring arrangement and a suitable film material.

In an advantageous embodiment of the sensor according to the invention, the sensor head is supported for displacement in a mount. This is especially advantageous, inasmuch as the position of the sensor head must be adjusted substantially only perpendicularly to the direction of transportation of the film. With a corresponding orientation of the mount, only a one-dimensional mobility of the sensor head is necessary, which can be realized in the simplest way in a linear displacement.

Basically, quite different drive means are possible for adjusting the position of the sensor head.

Especially advantageous is an adjustment of the position with the aid of a gas supply in the sensor head and with at least one outlet opening arranged on the measuring side. Via the gas supply and the outlet opening, a gas is directed under a predetermined pressure to the measuring object, namely the film. In this process, two effects overlie each other, so that an air cushion forms between the sensor head and the film. On the one hand, the gas pressure pushes the film away from the sensor head. On the other hand, however, the gas escaping laterally between the sensor head and the film and a thereby developing vacuum pulls up the film. If the gas pressure is adjusted to the arrangement and geometric configuration of the outlet opening as well as to the counterpressure of the film, an air cushion will form between the sensor head and the film. The thickness of this air cushion will determine the distance between the sensor head and the film. Especially advantageous with this procedure is that with a suitable selection of the operating parameters, an approximately constant distance adjusts itself between the sensor head and the film after a short buildup process. This distance adjusts itself practically during the entire measuring process.

The use of pressure gas as a medium for adjusting the position of the sensor head has also several positive marginal effects. On the one hand, the gas flowing through the sensor head to the film serves to stabilize temperature and cool the interior of the measuring arrangement, thereby also preventing largely temperature-induced measuring errors. On the other hand, depending on its composition, the gas may also be used for a further treatment of the film material.

It will be especially simple, cost-favorable, and therefore advantageous, when compressed air is used as gas. However, it would also be possible to use a protective gas that has a favorable effect on the film material.

The self-adjusting effect of the previously mentioned sensor arrangement may also be positively enhanced by a special constructional configuration of the sensor head. In this connection, it will be advantageous, when the measuring side of the sensor head is made plate-shaped and when a plurality of outlet openings extend, preferably concentric with the position of the sensor element, preferably in the center of the plate. In this instance, a relatively large air cushion is able to develop in the region of the sensor element.

Providing on the measuring side in the plate of the sensor head grooves or slots in which the outlet openings terminate can regulate the suction effect between the plate and the film. Depending on the orientation of the grooves and slots, such a sensor head exhibits a different behavior when adjusting its position. In all, it is thus possible to adjust the distance between the sensor head and the film with a predetermined counterpressure of the film, advantageously via the gas pressure, in connection with the dimensioning and arrangement of the outlet openings, as well as the dimensioning, arrangement and orientation of the grooves or slots.

In an advantageous embodiment of the sensor according to the invention, a tube arranged on the end side of the sensor head presents itself as a gas supply. Additionally, it will be of advantage, when the mount supports the sensor head for displacement by means of the tube. With respect to a self-adjustment of the position of the sensor head, the bearing of the sensor head or the tube should have as little friction as possible. A preferred possibility consists in arranging the sensor head in its mount by means of air bearings, so that the sensor head is displaceable substantially free of friction. To this end, the mount could comprise a guide tube for the tube mounting the sensor head, whose wall would contain passageways for introducing air. In this instance, the tube would be able to slide forward and back quasi on an air cushion within the guide tube.

In addition to the fine adjustment of the sensor head position, the mount for the sensor head could comprise an adjustment device for a coarse adjustment of the sensor head position and for "stiffening" the mount of the sensor head. The stiffening is intended to effect a damping of the system, which suppresses a high-frequency movement of the sensor head. Such an adjustment device could advantageously comprise a controlled drive. In this connection, the spacing between the sensor head and film will serve as a controlled variable. To automate likewise the coarse adjustment of the sensor head position as much as possible, the sensor of the present invention could comprise for a noncontacting thickness gauging an additional distance sensor. This distance sensor could operate, for example, by capacitance, induction, or by the ultrasound measuring principle. However, other measuring methods would also be possible as a function of the film material, for example, the optical measuring principle. Since the distance sensor is intended to serve for the coarse adjustment of the sensor head, it will be advantageous to arrange the distance sensor itself on the sensor head.

In the same manner as it is possible to use quite different drive means for adjusting the position of the sensor head, it will likewise be possible to use different drive configurations for the adjustment device.

The drive of the adjustment device may be, for example, pneumatic, which is especially advantageous in combination with a position adjustment of the sensor head with the aid of a gas supply in the sensor head. In the case of the sensor arrangement already described in this connection, the guide tube may accommodate to this end a pressure chamber, through which the tube mounting the sensor head extends. The tube could be provided with a pressure plate arranged in the region of the pressure chamber and oriented perpendicularly to the direction of movement of the sensor head, so that the pressure plate divides the pressure chamber into two sectional chambers. If each of the sectional chambers is provided with a connection to a gas line that extends into the sensor head, changes in the pressure conditions upstream of the sensor head and, thus, changes in the spacing between the sensor head and the film will become directly effective on the pressure conditions in the two sectional chambers of the pressure chamber. A corresponding connection of the two sectional chambers to the gas lines will permit counteracting a high-frequency movement of the sensor head and, thus, make it possible to realize a kind of damping and stabilization of the position of the sensor head.

However, the drive of the adjustment device may also be electric or magnetic. The drive may be, for example, a piezomotor or even a spindle in the case of a mechanical variant.

Damping the mount of the sensor head or suppressing very high-frequency movements of the sensor head will be especially important, when line connections are provided for supplying energy to the sensor head and/or for transmitting signals between the sensor head and an evaluation/control unit. In practice, these line connections may be realized by very thin coaxial cables that affect the movement of the sensor head as little as possible, but yet represent a mechanical coupling between the displaceably mounted sensor head and a stationary sensor element. Such line connections are particularly susceptible to high-frequency motions. During a damping of the system, i.e. by suppressing high-frequency motions, it will, however, be possible to eliminate this weak spot of the sensor according to the invention to a great extent.

In a particularly advantageous variant of the sensor according to the invention, energy is supplied to the sensor in a noncontacting manner, i.e., without a corresponding line connection between the movably mounted sensor head and a stationary sensor element. To this end, the energy could be inductively supplied by the transformer principle. Furthermore, when the signal transmission between the sensor head and an evaluation/control unit is likewise noncontacting, there will no longer be a mechanical coupling between the sensor head and the stationary sensor element, so that the sensor head is allowed to move unhindered. Likewise, in this instance a line break can no longer occur due to high-frequency movements of the sensor head. Between the sensor head and the evaluation/control unit, the signals may be transmitted by optics, induction or capacitance. It is especially advantageous to use a transmitter-receiver arrangement for transmitting signals. If this transmitter-receiver arrangement has a corresponding modulation device, it will be possible to apply to the signals being transmitted signal modulation methods as are known from transmitting signals, such as pulse-code modulation, frequency modulation, and amplitude modulation, so that it becomes likewise possible to ensure a certain insusceptibility to errors during the signal transmission. In any event, it is advantageous to amplify the measuring signals with the aid of a preamplifier before transmitting signals from the sensor head to the evaluation-control unit.

With respect to the evaluation/control unit as used within the scope of the sensor according to the invention, it should also be remarked that this unit might in part be integrated in the sensor head. For example, the sensor head may already accommodate an oscillating circuit as a part of the evaluation circuit. The evaluation/control unit is intended to evaluate primarily the measuring signals, i.e., to determine the thickness of the film. In addition, however, it is also possible to determine the spacing between the sensor head and the film and to use it for adjusting the drive of the adjustment device. The evaluation/control unit could contain in addition electronic equipment for monitoring the mounting of the sensor head, controlling the operation of the sensor as whole, for example, for controlling the gas pressure, and for associating the measured thickness values to the measuring location, i.e., to the position on the film. To this end, one may provide in addition two timers that also acquire in addition to the measured thickness values time information, which may be used for determining the measuring location.

There exist various possibilities of improving and further developing the present invention in an advantageous manner. To this end, reference may be made to the following detailed description of an embodiment of the invention with reference to the drawing.

BRIEF DESCRIPTION OF THE DRAWINGS

In conjunction with the description of the preferred embodiment of the invention, together with other preferred embodiments and further developments of the teaching, reference is made to the accompanying drawings, in which.

DETAILED DESCRIPTION OF THE PREFERRED EMBODIMENTS

Figure 1:
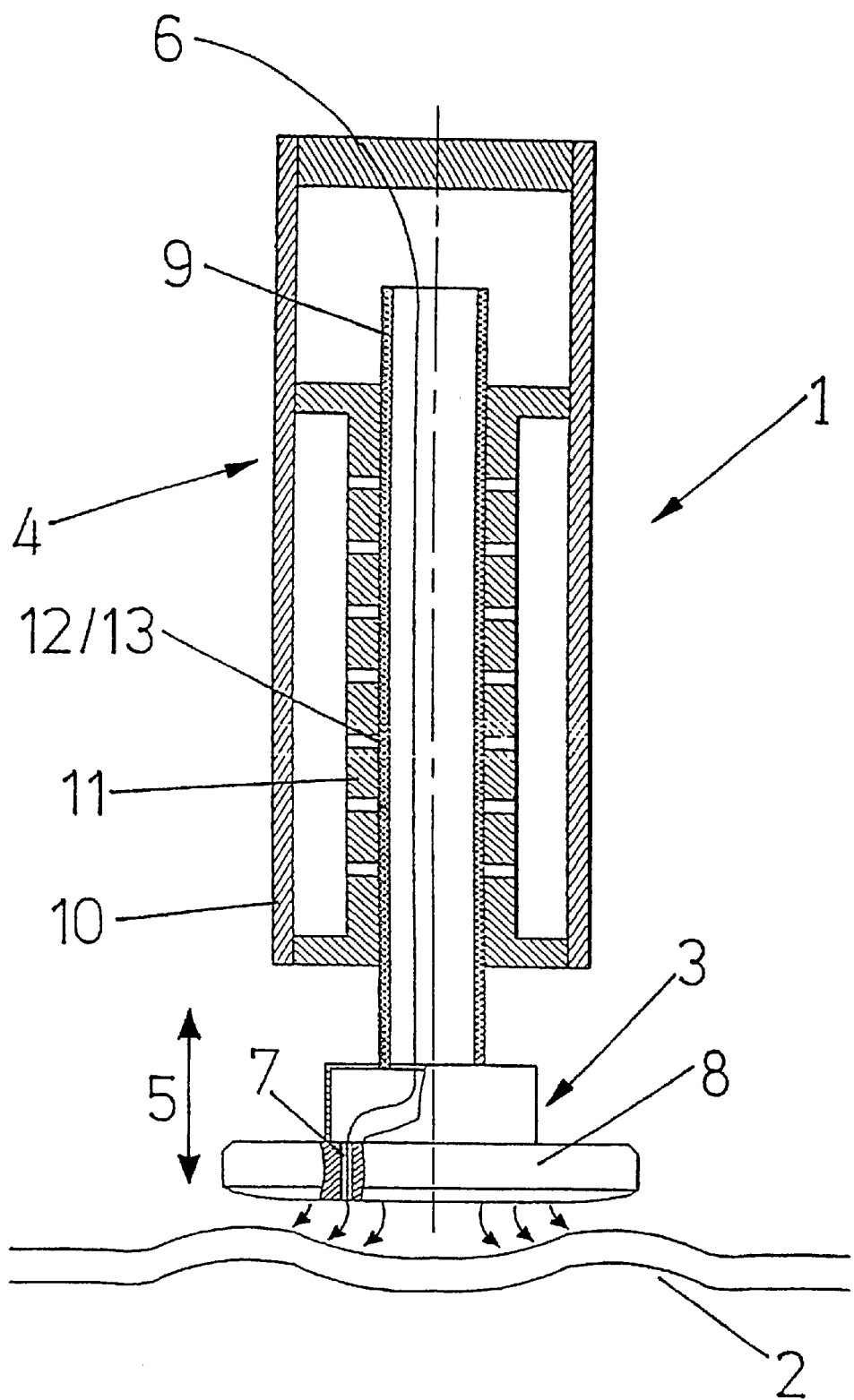
FIG. 1 is an axially sectioned view of a sensor according to the invention for noncontacting thickness gauging on films.

A sensor 1 is especially suited for noncontacting thickness gauging on blown films. To produce such films, a heated raw material is extruded and blown at the same time. The thickness is gauged with the aid of sensor 1 of the present invention during the production process at a time, when a film material 2 is not yet completely cooled and solidified. Such thickness measurements are performed for a quality control during the production process, to detect early material-caused or process-caused production errors and to be able to take countermeasures. The noncontacting thickness gauging facilitates in this instance a quality control without adversely affecting the still deformable film in any way.

The illustrated sensor 1 comprises a sensor head 3 and a mount 4 for the sensor head.

In accordance with the invention, the sensor head comprises for gauging the thickness at least one sensor element (not shown in FIG. 1) that operates in a noncontacting manner in response to the physical properties of film 2. The position of sensor head 3 is adjustable in such a manner that the sensor head 3 is held during the entire measuring procedure at a predeterminable, at least largely constant distance from the film 2.

Within the scope of the sensor according to the invention, it is basically possible to use any noncontacting sensor element that is suitable for gauging thickness. The measuring method that is ultimately applied is dependent on the physical properties of film 2. It will be advantageous, when the sensor element furnishes distance-independent measuring results at least in a small distance range between sensor head 3 and film 2, and when the spacing between sensor head 3 and film 2 lies also within the distance range of the distance-independent measuring results. Only then will it be possible to perform measurements that are comparatively unsusceptible to errors.

In the present instance of gauging the thickness on blown films that are normally made from a plastic acting as a dielectric, the sensor 1 of the present invention comprises a capacitive sensor element for gauging the thickness.

The sensor head 3 of the illustrated sensor 1 is mounted for displacement in mount 4, which is indicated by double arrow 5. Accordingly, the sensor head 3 can be moved perpendicularly to the film 2 or to the direction of transportation of film 2. As an actuator of this movement and, thus, as a means for adjusting the position, the sensor head 3 comprises a gas supply 6 and a plurality of outlet openings 7 on the measuring side. In the illustrated embodiment, the measuring side of sensor head 3 is constructed in the form of a plate 8. Of outlet openings 7, only one is shown by way of example. In all, the outlet openings 7 are arranged in concentric relationship at a certain distance around the plate center, where the sensor element is located. Advantageously, the outlet openings 7 terminate in grooves or slots that are not shown in FIG. 1.

In the illustrated embodiment, compressed air flows through the sensor head 3 onto film 2. When suitably adapting pressure, number, arrangement, and geometry of outlet openings 7 and the grooves and slots, as well as the counterpressure of film 2 that advances past the sensor head 3, an air cushion will form in the region of the sensor element, namely the plate center, between sensor head 3 and film 2. This is due, on the one hand, to pressure exerted by the compressed air on film 2 and, on the other hand, on the vacuum between sensor head 3 or plate 8 and film in the edge regions of plate 8. Consequently, the relative position between the sensor head and film 2 is stabilized. After a short buildup phase, the spacing between sensor head 3 and film 2 is constant. This also applies during the transportation of film 2 in case of a possible fluttering of film 2. Consequently, a noncontacting and distance-independent thickness gauging is possible even on the advancing, not-yet solidified elastic film 2.

The compressed air exiting from sensor head 3 has in addition a cooling effect, so that the thickness measurements are conducted in a constant temperature range and that even measuring errors caused by temperature fluctuations are largely avoided.

In the embodiment of a sensor 1 according to the invention as illustrated in FIG. 1, the sensor head 3 is arranged at the end of a tube 9 that serves at the same time as a gas supply 6 to sensor head 3. The sensor head 3 is supported, via tube 9, for displacement in mount 4. More specifically, the mount 4 comprises a casing 10 with a guide tube 11 for tube 9. For introducing air, the wall of guide tube 11 contains openings 12 that ultimately serve as an air bearing 13 for tube 9 and, thus, for sensor head 3. Via the air bearings 13, the sensor head 3 is supported in mount 4 for displacement substantially free of friction.

Figure 2:
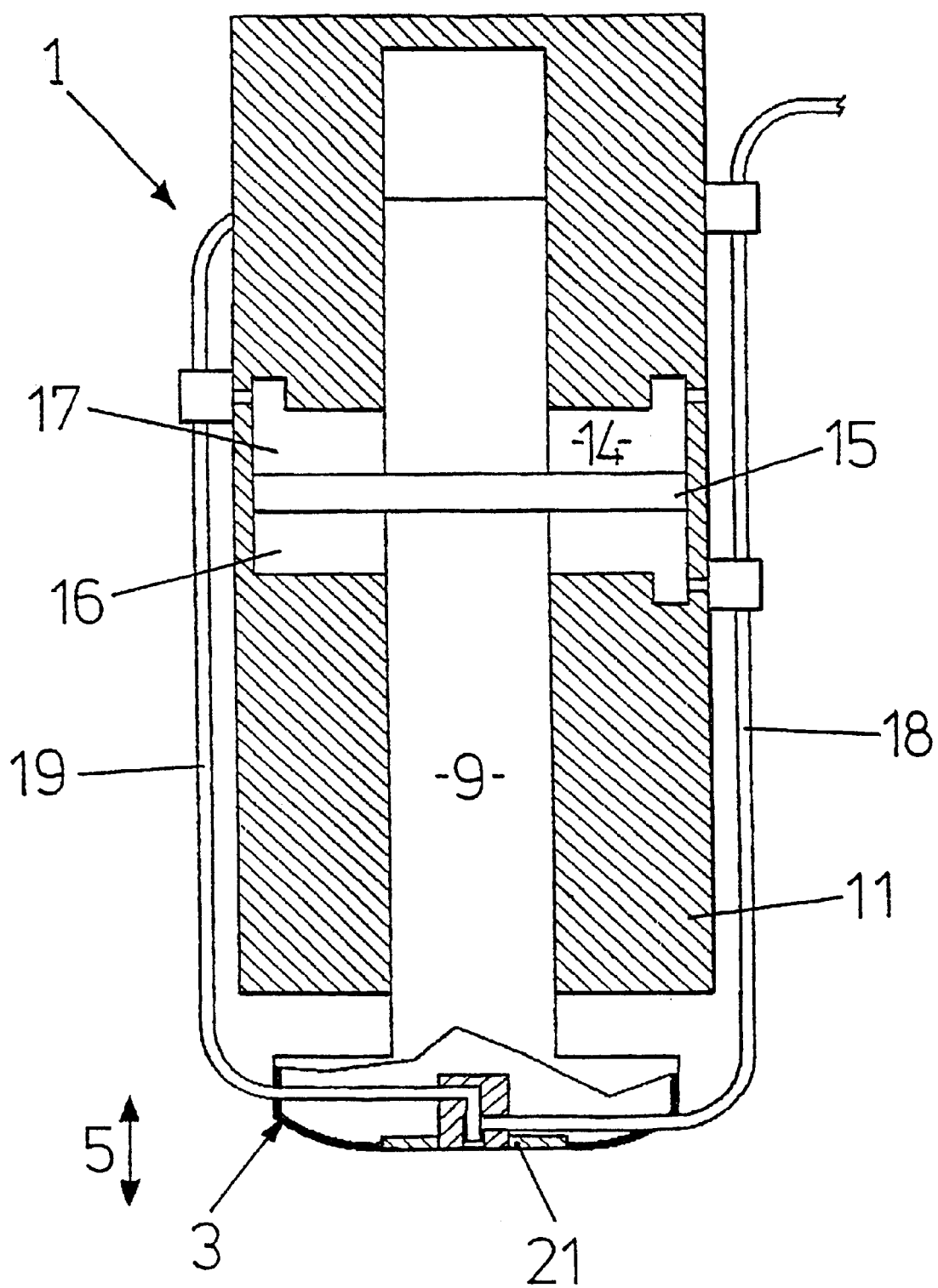
FIG. 2 shows a sensor of the present invention with a pneumatically operating adjustment device.

In addition, the mount of sensor 1 could also comprise an adjustment device for a coarse adjustment and stabilization of the position of the sensor head. FIG. 2 shows such a sensor 1 with a pneumatically operating adjustment device. In this embodiment, the sensor head 3 is likewise supported for displacement, which is indicated by double arrow 5. To this end, the measuring head 3 is mounted on a tube 9, which is supported for displacement in a guide tube 11. The guide tube 11 accommodates a pressure chamber 14 through which the tube 9 extends. In the region of pressure chamber 14, the tube 9 mounts a pressure plate 15 that is dimensioned such that it divides pressure chamber 14 into two sectional chambers 16 and 17. Each of the two sectional chambers 16 and 17 connects to a gas line 18, 19 each of which extends into sensor head 3. As a result, a dynamic pressure that builds up between the sensor head 3 and the film not shown in FIG. 2, acts directly upon the pressures prevailing in sectional chambers 16 and 17. The dynamic pressure is again dependent on the distance between the measuring head 3 and the film. A change in the distance will result in a pressure difference between the pressures in the two sectional chambers 16 and 17. As a result, a force is exerted on pressure plate 15 and, thus, on tube 9. A corresponding connection of sectional chambers 16 and 17 to gas lines 18 and 19 thus permits suppression of high-frequency movements of the measuring head 3.

In connection with FIG. 2, it should be noted that same is only a schematic illustration that is intended to make clear that it is possible to achieve by way of pneumatics a coarse adjustment of the position of sensor head 3 and even a damping of the movement of sensor head 3.

Figure 3:
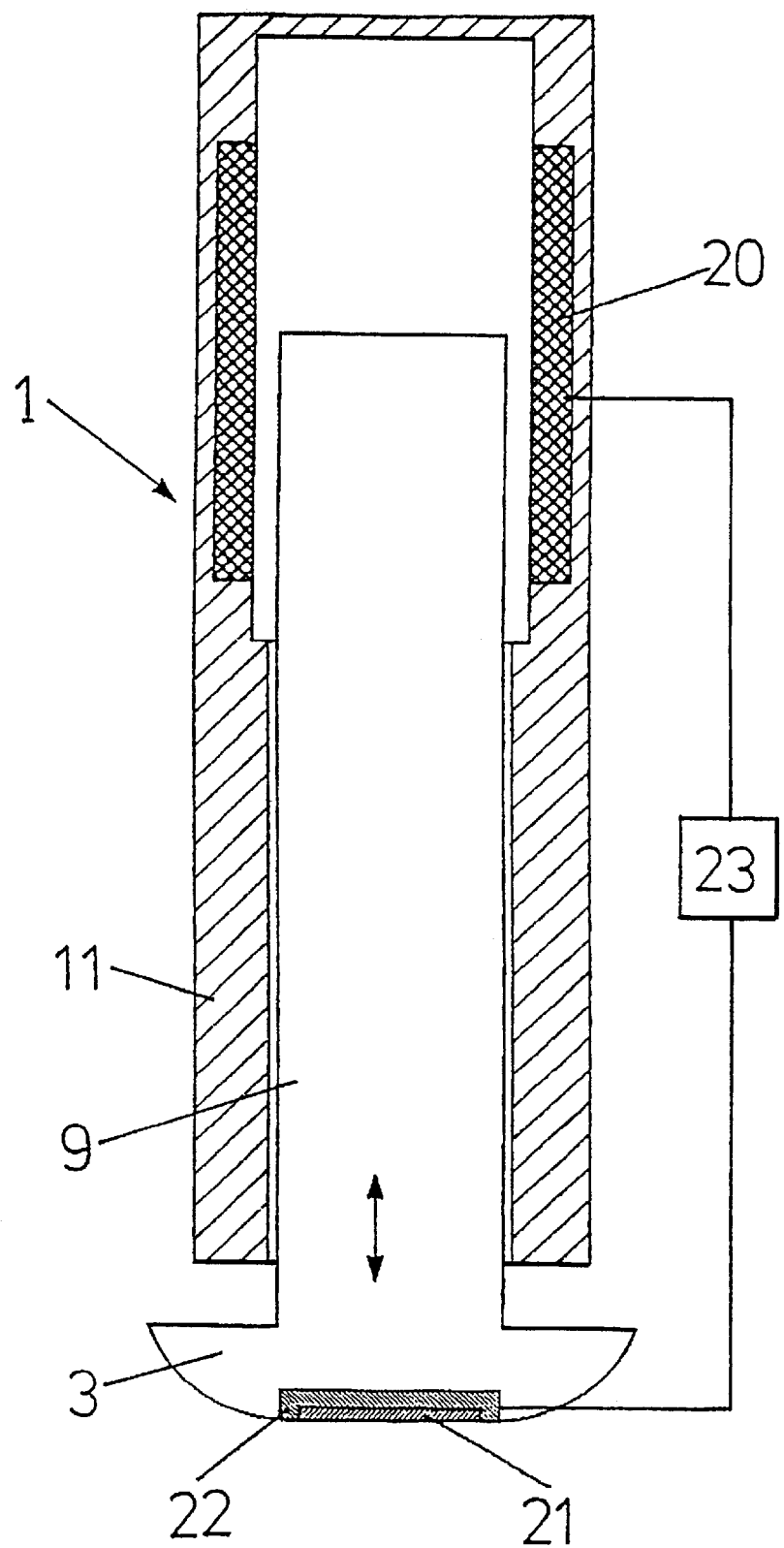
FIG. 3 shows a further sensor of the present invention with an adjustment device comprising an actuator.

FIG. 3 is intended to illustrate that the position of sensor head 3 can also be stabilized with the aid of an adjustment device comprising an actuator. To this end, the mount 4 of sensor head 3 mounts an actuator 20 that facilitates displacement of the tube 9 inside guide tube 11. The actuator 20 may be an electrically or even magnetically operated drive. Likewise suitable as a mechanical drive is, for example, a piezomotor or a spindle. For adjusting the position of sensor head 3, the sensor 1 comprises in addition to a sensor element 21 that gauges the thickness of the film, a distance sensor 22, that determines the spacing between sensor head 3 and the film. This distance value is used as a controlled variable for actuator 20, which is indicated in FIG. 3 by a proportional-integral-differential (PID) controller 23.

In connection with FIG. 3, it should also be remarked that in this illustration a sensor-in-sensor system is realized in that the distance sensor 22 is arranged around the sensor element 21 that gauges the thickness of the film. In this manner, it is ensured that the distance sensor 22 determines indeed the spacing that is relevant for the measurement between sensor element 21 and the film.

With the aid of the adjustment devices as described with reference to FIGS. 2 and 3, it is possible, as has already been mentioned several times, to perform both a coarse adjustment of the position of the sensor head and a stabilization of this position, i.e., a suppression of high-frequency movements of the sensor head. This will be especially important, when the energy supply and/or the signal transmission from the sensor head to an evaluation/control circuit occurs via line connections. Such line connections must be so thin and filigrained that they interfere with the movement of the sensor head as little as possible. Consequently, they exhibit only very little mechanical stability, so that they rapidly break in particular because of high-frequency movements.

Figure 4:
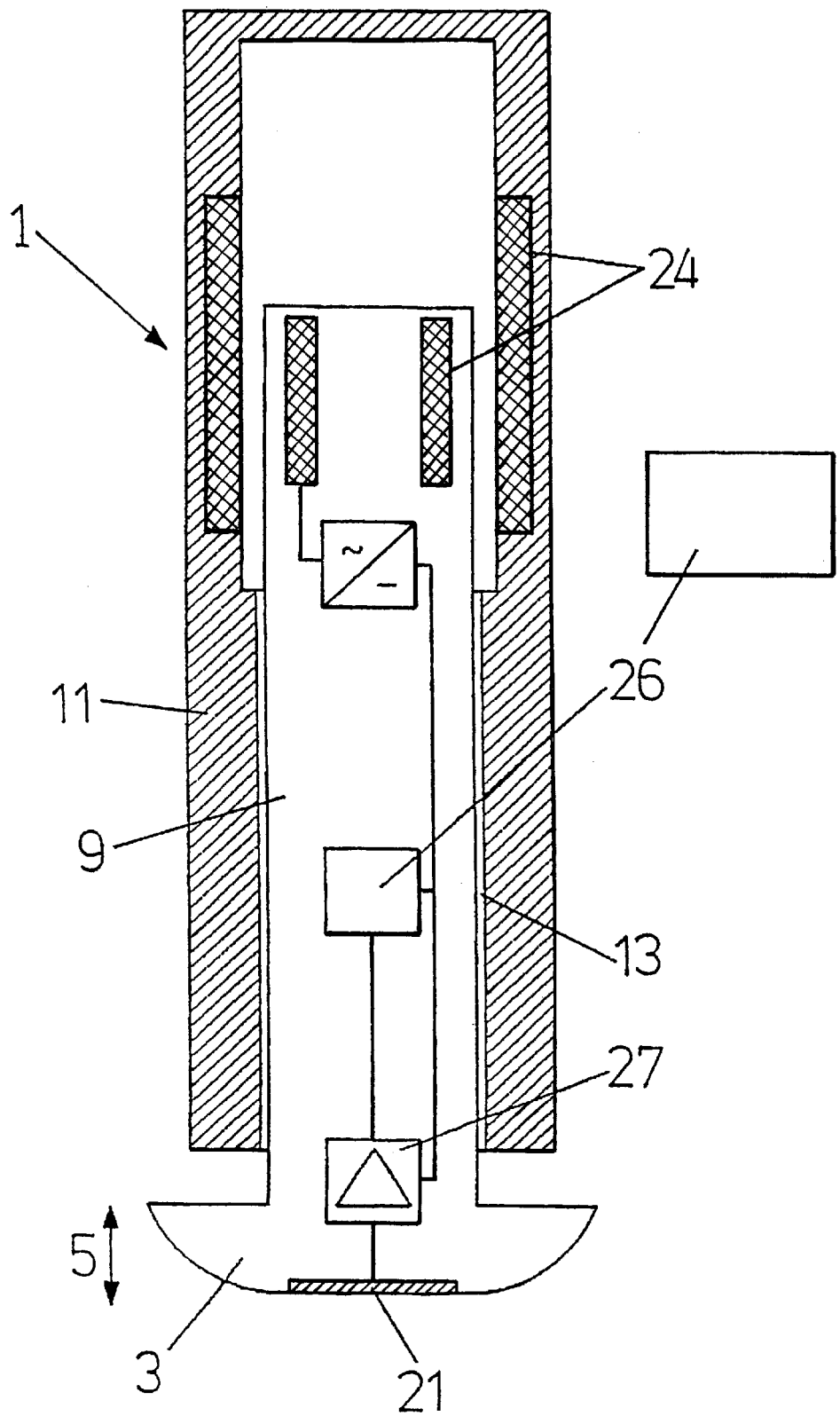
FIG. 4 shows a sensor of the present invention, wherein the energy supply and signal transmission are noncontacting.

FIG. 4 illustrates an embodiment of the sensor 1 according to the invention, wherein the energy supply is noncontacting, namely inductive by the transformer principle. To this end, a coil 24 is arranged both in the region of guide tube 11 and in the corresponding region of tube 9. Via this coil, energy is supplied into the sensor head 3. The transmission of measuring signals from sensor head 3 to an evaluation/control unit 25 that is arranged externally, for example, in the casing of sensor 1, is in this instance likewise noncontacting with the aid of a transmitter-receiver device 26. However, it would likewise be possible to transmit the signals, for example, by way of optics. In the region of sensor head 3 or adjacent tube 9, a part of the evaluation circuit is arranged, which comprises a preamplifier 27. The amplified signal is then transmitted to evaluation/control circuit 25. To lessen the error proneness of such a signal transmission, the measuring signal may also undergo a previous modulation, for example, a pulse-code modulation, a frequency modulation, or even an amplitude modulation.

In summary, it should be emphasized at this point one more time that in the represented embodiments of sensors according to the invention for noncontacting thickness gauging of films, it is common to begin with a coarse adjustment of the spacing between the sensor head and the film with the aid of an additional distance sensor. The fine adjustment of the spacing between the sensor head and the film will then occur automatically, in that with the aid of compressed air a small air gap or an air cushion is generated between the sensor head and the film, the width of which is preferably in the range of the distance-independent measuring results of the thickness gauging sensor element. To adjust the air gap, compressed air is directed via the sensor head onto the film, so that a vacuum develops at the edge of the sensor head. Consequently, the film is attracted, without however contacting the sensor head itself. In addition, the sensor head is supported free of friction inside the mount of the sensor, thus modifying not only the position of the film itself, but also the position of the sensor head. In the sensor of the present invention, the spacing between the sensor head and the film is thus maintained constant.

As regards further characteristic features not shown in the Figures, the background portion of the specification is herewith incorporated by reference.

Finally, it should be emphasized that the teaching of the present invention is suitable not only for thickness gauging on blown films, but is also suited in general for thickness gauging of films on any desired material.

What is claimed is:

1. A sensor for the non-contacting thickness gauging of a film, comprising a sensor head which includes a bottom plate, and at least one non-contacting sensor element mounted on the bottom plate and which is capable of gauging the thickness of the film from the physical properties of the film when the film is located adjacent and spaced below the bottom plate, and a plurality of gas outlets extending through the bottom plate and directed toward the film, with the outlets arranged to encircle the sensor element, a mount mounting the sensor head for movement toward and away from the film, means for adjusting the position of the sensor head in the mount and comprising a gas supply connected to the gas outlets so that a gas flow is directed toward the film, and wherein a fine adjustment of the spacing between the bottom plate of the sensor head and the film occurs automatically by means of the gas flow, and wherein the gas flow generates a vacuum about the sensor element which acts to lift the film without contacting the bottom plate so that during the measuring procedure a predeterminable and essentially constant relative position is maintained between the bottom plate and the film in spite of any random movement of the film toward and away from the bottom plate, and a separate adjustment device for the coarse adjustment of the position of the sensor head in the mount, said separate adjustment device including a distance measuring sensor mounted on said sensor head and a drive for moving the sensor head in the mount in response to a signal from the distance measuring sensor.

2. The sensor as defined in claim 1, wherein the sensor element is configured to provide distance independent measuring results in a small distance range between the sensor head and the film.

3. The sensor as defined in claim 1, wherein the sensor element is selected from the group consisting of a capacitance sensor, an inductive sensor, and an optical sensor.

4. The sensor as defined in claim 1, wherein the gas supply comprises a compressed air supply.

5. The sensor as defined in claim 1, wherein the gas outlets terminate in grooves formed in the bottom plate.

6. The sensor as defined in claim 1, wherein the mount mounting the sensor head includes a tube connected to the sensor head and which is slideably received within a casing, and wherein the gas supply extends through the tube.

7. The sensor as defined in claim 6, wherein the mount further comprises an air bearing between the tube and the casing to minimize friction therebetween.

8. The sensor as defined in claim 1, wherein the distance measuring sensor is selected from the group consisting of a capacitance sensor, an inductive sensor, an optical sensor, and an ultrasound device.

9. The sensor as defined in claim 1, wherein the drive for moving the sensor head is selected from the group consisting of a pneumatic drive, an electric drive, a magnetic drive, a piezomotor, and a mechanical drive.

10. The sensor as defined in claim 1, wherein the mount mounting the sensor head includes a tube connected to the sensor head and which is slideably received within a casing, wherein the gas supply extends through the tube, and wherein the drive of the separate adjustment device comprises a pressure chamber formed between the tube and the casing, a pressure plate mounted to the tube and positioned within the pressure chamber so as to divide the pressure chamber into upper and lower chamber sections, with each chamber section connected to a gas line which extends into the sensor head.

11. The sensor as defined in claim 1, wherein the drive for moving the sensor head includes an inductive energy supply for transmitting electrical energy to the distance measuring sensor.

12. The sensor as defined in claim 1, wherein the signal from the distance measuring sensor is transmitted to the drive by a transmission selected from the group consisting of an optical transmission, an inductive transmission, and a compacitive transmission.

13. The sensor as defined in claim 1 wherein the signal from the distance measuring sensor is transmitted to the drive by a transmitter-receiver device.

* * * * *